United States Patent [19]

Fields et al.

[11] Patent Number: 4,638,072
[45] Date of Patent: Jan. 20, 1987

[54] DISUBSTITUTED MALEIC ANHYDRIDE COMPOUNDS

[75] Inventors: Ellis K. Fields, River Forest; Mark L. Winzenburg, Naperville; Steven J. Behrend, Glendale Heights, all of Ill.

[73] Assignee: Standard Oil Company (Indiana), Chicago, Ill.

[21] Appl. No.: 807,677

[22] Filed: Dec. 11, 1985

Related U.S. Application Data

[62] Division of Ser. No. 630,361, Jul. 12, 1984, Pat. No. 4,596,867.

[51] Int. Cl.$^4$ .................. C07D 307/77; C07D 493/04
[52] U.S. Cl. .................................... 549/234; 549/235
[58] Field of Search ................................ 549/234, 235

[56] References Cited

FOREIGN PATENT DOCUMENTS 3125057  1/1983  Fed. Rep. of Germany .

OTHER PUBLICATIONS

Edwards et al., Chemical Abstracts, vol 73 (1970) 25170a.

Gruetzmacher et al., Chemical Abstracts, vol. 93 (1980) 95,043y.

Sargent et al., J. Chem. Soc. (1964) p. 5544.

Primary Examiner—Richard L. Raymond
Attorney, Agent, or Firm—James R. Henes; William T. McClain; William H. Magidson

[57] ABSTRACT

Di-substituted maleic anhydride compounds are disclosed of the structural formula

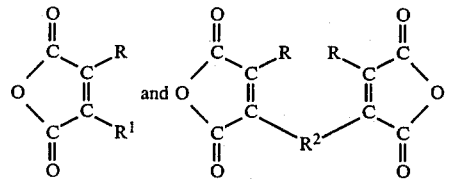

wherein R and $R^1$ are selected from the group consisting of aliphatic and phenyl moieties, and $R^2$ is a divalent aromatic moiety. Polyamide-imide polymers, polyimide polymers and vinyl copolymers derived therefrom are also disclosed.

3 Claims, No Drawings

DISUBSTITUTED MALEIC ANHYDRIDE COMPOUNDS

This is a division of application Ser. No. 630,361 filed July 12, 1984, now U.S. Pat. No. 4,596,867.

This invention relates to di-substituted maleic anhydride compounds of the structures

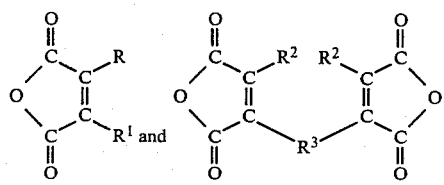

wherein R, $R^1$, and $R^2$ are aliphatic or phenyl moieties and $R^3$ is a divalent organo moiety. R, $R^1$, and $R^2$ are individually selected from the following groups: alkyl groups of 1 to 10 carbon atoms; phenyl groups wherein the phenyl groups are optionally substituted with substituents selected from the group consisting of halides, alkyl groups of 1 to 5 carbon atoms, phenyl groups, naphthyl groups, $-NO_2$, $-NHCOCH_3$, $-NH_2$, $-OCOCH_3$, $-OH$, $-OCH_3$, $-CH=CH_2$, $-CO_2H$, $-C(O)O(O)C-$; $-CH=CHR'$, and wherein $R'$ is selected from the group consisting of phenyl optionally substituted as described above, thienyl, furyl; phenyl, naphthyl, indole-2-yl, thienyl and $-S-C_6H_5$ groups, optionally substituted with substituents selected from the group consisting of $-CH_3$ and $-CO_2H$; and $-SO_2C_6H_5$. $R^3$ is a divalent aromatic moiety selected from the group consisting of $-C_6H_4-$, $-C_6H_2(CH_3)_2-$, $-C_6H_4-C_6H_4-$, $-C_6H_4-O-C_6H_4-$, $-C_6H_4-CH_2-C_6H_4-$, $-C_6H_4-C(CH_3)_2-C_6H_4-$, $-C_6H_4-N=N-C_6H_4-$, $-C_{10}H_6-$, and $-SC_6H_4S-$.

This invention also relates to substituted phenanthrene anhydride compounds of the structure

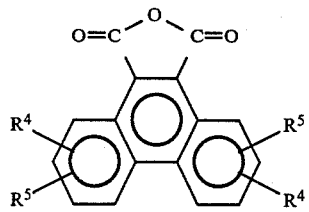

and the dibenzanthracene dianhydride compounds of the structure

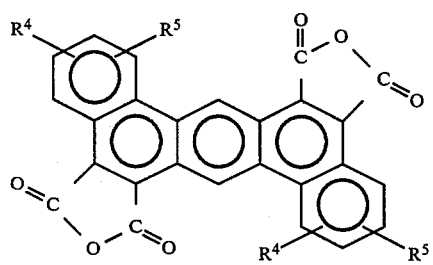

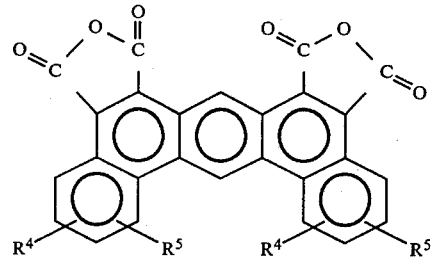

wherein $R^4$ and $R^5$ are individually selected from the following groups: hydrogen; alkyl groups of 1 to 10 carbon atoms; phenyl groups, naphthyl groups, $-NO_2$, $-NHCOCH_3$, $-NH_2$, $-OCOCH_3$, $-OH$, $-OCH_3$, $-CH=CH_2$, $CO_2CH_3$, and $-CO_2H$.

This invention also relates to novel polyamide-imides prepared from the novel di-substituted maleic anhydride compositions wherein R is an aromatic group of up to 20 carbon atoms and $R^1$ is carboxy-substituted aryl group of up to 20 carbon atoms, and to novel polyimides prepared from the novel bis(di-substituted maleic anhydride) compositions wherein $R^2$ is selected from the following groups: (a) alkyl groups of 1 to 10 carbon atoms; (b) phenyl groups wherein the phenyl groups are optionally substituted with substituents selected from the group consisting of halides, alkyl groups of 1 to 5 carbon atoms, phenyl groups, naphthyl groups, $-NO_2$, $-NHCOCH_3$, $-NH_2$, $-OCOCH_3$, $-OH$, $-OCH_3$, $-CH=CH_2$, $-CO_2H$, and $-C(O)O(O)C-$; $-CH=CHR'$ wherein $R'$ is selected from the group consisting of phenyl optionally substituted as described above, and thienyl, furyl; (c) naphthyl, phenanthryl, indole-2-yl, furyl, thienyl, $-S-C_6H_5$ and $-SO_2C_6H_5$ groups optionally substituted with substituents selected from the group consisting of $-CH_3$ and $-CO_2H$; and $R^3$ is a divalent aromatic moiety selected from the group consisting of $-C_6H_4-$, $-C_6H_2(CH_3)_2-$, $-C_6H_4-C_6H_4-$, $-C_6H_4-O-C_6H_4-$, $-C_6H_4-CH_2-C_6H_4-$, $-C_6H_4-C(CH_3)_2-C_6H_4-$, $-C_6H_4-N=N-C_6H_4-$, $-C_{10}H_6-$, and $-SC_6H_4S-$.

BACKGROUND OF THE INVENTION

It is known to make diphenylmaleic anhydride by condensation of potassium benzoylformate with phenylacetic acid (C. P. Koelsch, et al., *J. Org. Chem.*, 6, 684, (1941)). The synthesis of phenanthrene-9,10-dicarboxylic anhydride from diphenyl maleic anhydride in air is also reported (M. V. Sargent, et al. *J. Chem. Soc.*, 5544, (1964)). However, the techniques demonstrated in these reports have not been extended to the synthesis of multifunctional compounds such as the di-substituted maleic anhydride compounds and bis(di-substituted maleic anhydide) compounds of this invention which are capable of forming amide-imide polymers, as well as other polymers.

It is also known to make dianhydrides from maleic anhydride as is taught in commonly-assigned Ser. No. 294,322, now U.S. Pat. No. 4,360,657, and Ser. No. 386,891, now abandoned, which are hereby incorporated by reference. It is also known to make polyimides from dianhydrides and aromatic amines. This is disclosed in U.S. Pat. No. 3,179,634 (1965). British Patent Specification No. 570,858 discloses various processes for making fiber-forming polymers.

In reviewing these references it is clear that the synthesis of di-substituted maleic anhydride and bis(di-substituted maleic anhydride) compounds which are capable of forming amide-imide polymers, polyimides, and vinyl co-polymers has not been contemplated in the prior art. Also, the prior art has not contemplated the preparation of di-substituted maleic anhydride compounds of the structures

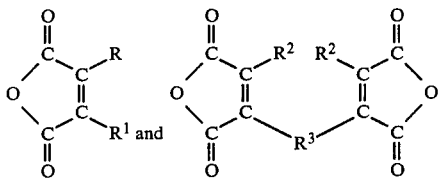

wherein R, $R^1$, $R^2$, and $R^3$ are defined as heretofore.

The general object of this invention is to provide novel compounds of maleic anhydride structure and novel derivatives of these compounds which are potentially difunctional in structure and to provide novel amide-imide polymers and polyimides. A more specific object of this invention is to provide amide-imide polymers, vinyl polymers, and polyimides from 2-phenyl-3-(p-carboxyphenyl)-maleic anhydride; 2-(m-carboxyphenyl)-3-phenylmaleic anhydride and 2-(o-carboxyphenyl)-3-phenylmaleic anhydride; 3-carboxyphenanthrene-9,10-dicarboxylic anhydride; 2,2'-(1,4-phenylene)-bis(3-methylmaleic)anhydride; 2,2'-(1,4-phenylene)-bis(3-phenylmaleic)anhydride; 2,2'-(1,4-phenylene)-bis(3-(2-phenylethenyl)maleic)anhydride; 2-vinylphenyl-3-phenylmaleic anhydride; 2,2'-(1,3-phenylene)-bis(3-phenylmaleic)anhydride; substituted 2,3-diphenylmaleic anhydrides. Another object of this invention is to provide simple procedures for the preparation of these novel maleic anhydride compounds and the polymers which can be prepared therefrom.

SUMMARY OF THE INVENTION

This invention relates to di-substituted maleic anhydride compounds of the structure:

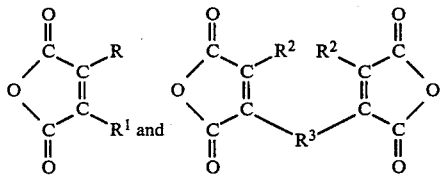

wherein R, $R^1$, and $R^2$ are aliphatic or phenyl moieties and $R^3$ is a divalent hydrocarbon moiety which can be substituted with sulfur, oxygen, nitrogen and hydrogen moieties. The invention also relates to amide-imide polymers and polyimides prepared from these maleic anhydride compounds and the methods of preparation thereof.

DETAILS OF THE INVENTION

This invention relates to di-substituted maleic anhydride compounds of the structure:

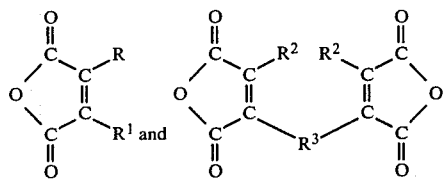

prepared by a modified Perkin condensation reaction wherein an alpha-keto acid of the formula $RCOCOOH$ or $R^2COCO_2H$ is reacted with a carboxylic acid of the formula $R^1CH_2COOH$ or $R^3(CH_2COOH)_2$ in the method of Koelsch, et al. J. Org. Chem. 6, 684 (1941). The acid of formula $R^1CH_2COOH$ or $R^3(CH_2CO_2H)_2$ requires two activated hydrogen on the alpha carbon. R, $R^1$, $R^2$, and $R^3$ are as defined heretofore.

For example, although R cannot be hydrogen, R can be a thienyl group, a furyl group or a selenophenyl group. If $R^1$ is a cyano group or a halogen, decomposition occurs under the conditions of the reaction. However, $R^1$ can be a phenyl group, a substituted phenyl group with substituents as previously stated, groups such as 2-naphthyl and substituted 2-naphthyl, and groups such as thienyl, furyl or selenophenyl groups.

Preparation of the di-substituted maleic anhydride compounds can be by reaction of the alpha-keto acid as the alkali metal salt. For example, in preparation of 2-phenyl-3-(p-carboxyphenyl)-maleic anhydride, potassium benzoylformate is condensed with p-carboxyphenylacetic acid. Benzoylformic acid can be prepared by oxidation of mandelic acid, the hydrolyzed condensation product of benzaldehyde with sodium cyanide. p-Carboxyphenylacetic acid can be prepared from p-tolunitrile by bromination, treatment with cyanide and hydrolysis. Mixed sodium and potassium salts of benzoylformic acid are condensed in refluxing acetic anhydride with the appropriate carboxylic acid formula $R^1CH_2COOH$. An alternate procedure is to react the alpha-keto acid with a slurry of an alkali metal salt of the selected substituted acetic acid in acetic anhydride according to the following equation.

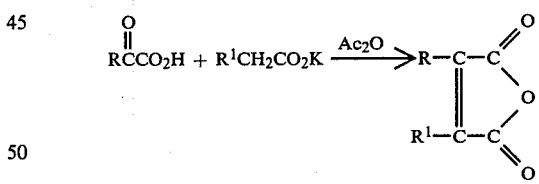

This is the preferred procedure if the alpha-keto acid is unstable to base or heat, such as the case of pyruvic acid. Moderate to good yields are obtained with this procedure. By contrast, heating a mixture of sodium or potassium pyruvate with a substituted acetic acid in acetic anhydride solution gives very low yields of the di-substituted maleic anhydride and much black decomposition product.

Substituted maleic anhydride compounds have been determined to be useful precursors for rust inhibitors, agricultural biocides, epoxy curing agents and surfactants and fluorescent dyes as taught by German Patent No. 2,419,765. The imides of these compounds with amines such as t-butylaniline or octadecylamine can yield soluble compounds useful as fluorescent dyes and markers.

Substituted maleic anhydride compounds are useful to prepare dianhydrides according to the following formula

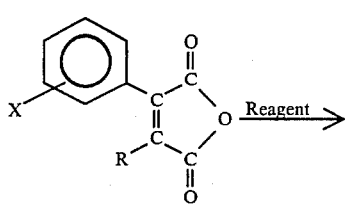

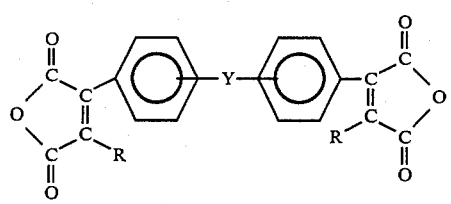

| X | Reagent | Y |
|---|---|---|
| NO$_2$ | Zn, NaOH | —N=N— |
| Br | Na$_2$S, CH$_3$CONMe$_2$ | —S— |
| OH | 1. Base<br>2. BrCH$_2$CH$_2$Br | —OCH$_2$CH$_2$O— |
| OH | ClCCl<br>∥<br>O | —OCO—<br>∥<br>O |
| NH$_2$ | CH$_3$COOH, NaBO$_3$ | —N=N— |
| OH | ClC—⟨O⟩—C—Cl<br>∥         ∥<br>O        O | —O$_2$C—⟨O⟩—CO$_2$— |
| NH$_2$ | ClC(CH$_2$)$_4$—C—Cl<br>∥              ∥<br>O             O | —HNC(CH$_2$)$_4$CNH—<br>∥                  ∥<br>O                 O | wherein the resulting dianhydrides contain linkages Y such as thio, azo, ether, carbonate, ester, amide, and the like, and said dianhydrides are useful for condensation with diamines to form polyimide resins.

This invention also relates to substituted phenanthrene anhydride compounds, substituted dibenzanthracene dianhydride compounds, and higher molecular weight polynuclear aromatic analogues of the following structures

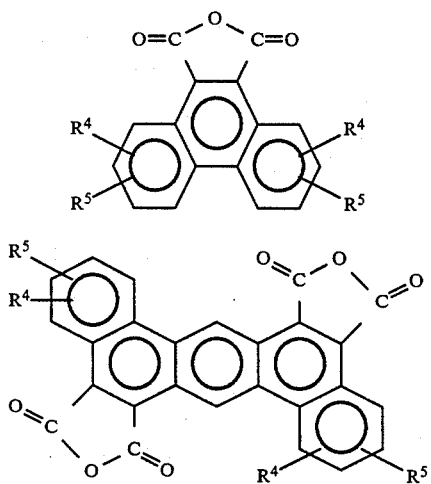

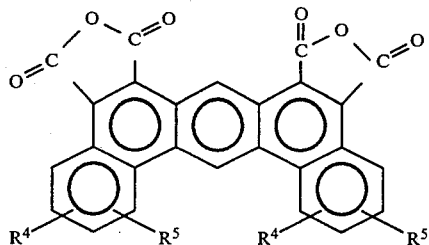

which can be prepared by photo-oxidation of the corresponding di-substituted maleic anhydride compounds and bis(di-substituted maleic anhydride) compounds.

For example, 3-carboxyphenanthrene-9,10-dicarboxylic anhydride of this invention is prepared according to the following formula.

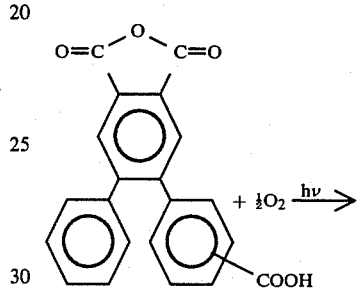

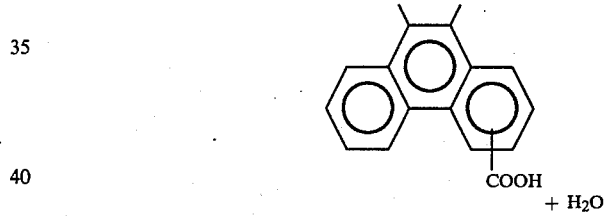

+ H$_2$O

The substituted phenanthrene anhydride, substituted dibenzanthracene dianhydride, and higher molecular weight polynuclear aromatic anhydride compounds of this type can be prepared by loss of hydrogen from a sp2 hybridized carbon atom and bond formation to another such carbon atom. For this reason the preparation of the polynuclear aromatic anhydride compounds of this invention by photooxidation requires that the R, R$^1$, R$^2$, and R$^3$ components of the corresponding maleic anhydride compounds be aromatic in character. The maleic anhydride compounds of this invention wherein R, R$^1$, R$^2$, or R$^3$ are alkyl or substituted alkyl have sp3 hybridized carbon atoms alpha to the olefinic carbon of the maleic anhydride compound and do not react to give phenanthrene anhydride, dibenzanthracene anhydride, and higher molecular weight polynuclear aromatic anhydride compounds.

Preparation of the polynuclear aromatic anhydride compounds of this invention can be by irradiation with any suitable light source such as sunlight, a sunlamp, an ordinary incandescent lamp, or a mercury vapor arc lamp. Air or oxygen is bubbled through a solution of the maleic anhydride compound dissolved in a suitable inert solvent such as acetone, cyclohexanone, methylethyl ketone, or acetophenone containing a small amount of iodine to catalyze the reaction. The reaction vessel can be any material which allows passage of the near ultraviolet light from the lamp to the reaction.

Phenanthrene anhydride compounds have been determined to be useful as precursors to phthalocyanine type pigments and dyes.

Novel amide-imide polymers and polyimide polymers have been prepared from the substituted maleic anhydride compounds and corresponding substituted phenanthrene anhydride and dibenzanthracene compounds by a simple condensation reaction with a difunctional amine and requiring only the application of heat. Temperature range is from about 80° C. to about 250° C., preferably from about 160° C. to about 220° C.

The polymers of this invention have outstanding resistance to heat and solvents, high mechanical strength and excellent electrical properties.

The polymers of this invention are formed by reacting the anhydride-acids and dianhydrides of this invention with a difunctional amine of the general formula $NH_2-R^8-NH_2$ wherein $R^8$ is selected from the group consisting of $-R^6-$ and $-R^6-X-R^7-$ wherein $R^6$ and $R^7$ are individually selected from divalent groups selected from the group consisting of from 2 to 20 methylene groups and 1 to 3 phenylene groups and X is selected from the group consisting of $-O-$, $-S-$, $-SO_2-$ and $-CH_2-$.

It is known that the reaction between the difunctional amine and the anhydride can be carried out either in bulk or in an inert polar carrier medium. In the bulk process, apparently because reactivity is low unless the mixture is melted, it is necessary to heat the reaction mixture to an elevated temperature on the order of 100° C. to 200° C. to induce any reaction at all between the two reagents. In most cases, at least about 120° C. is used and it is preferred to heat at about 160° C. if the reaction is to be comprised in a reasonable time. If an inert polar carrier medium is to be used, it is preferred that N-methylpyrrolidinone (NMP) be employed. Dimethylacetamide, dimethylformamide, and a pyridine-toluene 50:50 mixture can also be used. If N-methylpyrrolidinone (NMP) is used as a carrier, it is specifically recommended to heat the solution at reflux temperature, i.e., near 202° C.

It is known that production of the imide by reaction of a diamine with an anhydride is accompanied by the formation of water. The water of reaction can be moved by addition of an aromatic compound such as xylene or toluene which forms an azeotrope with water which can then be distilled. Other side reaction products can be removed by precipitation of the imide and other separation techniques.

The process by which novel polymer compositions of this invention are prepared comprises (a) dissolving a difunctional amine and the maleic anhydride compound in an inert solvent to form a solution containing about 1 mole of anhydride for each mole of amine, (b) heating the solution at a temperature not in excess of 250° C. to form a condensation product in which the amine groups have substantially reacted. Conventional product separation techniques are used to obtain and purify the resulting polymer.

In order to facilitate a clear understanding of the invention, the following specific embodiments are described in detail. It should be understood, however, that the detailed expositions of the instant invention, while indicating preferred embodiments, are given by way of illustration only since various changes and modifications within the spirit and scope of the invention will become apparent to those skilled in the art from this detailed description.

The formulations in each of the following examples have been confirmed by elemental analysis. These analyses have been stated in representative examples.

EXAMPLE I

Preparation of 2-(4-carboxyphenyl)-3-phenylmaleic anhydride (I) was as follows. A 500 ml flask was charged with 4-carboxyphenylacetic acid (20 g, 0.11 mole), 200 ml of acetic anhydride, and mixed sodium/potassium salt of benzoylformic acid (20.7 g, 0.11 mole). Warming resulted in a mildly exothermic reaction. The mixture was stirred at reflux for three hours, cooled to room temperature, and quenched by careful addition of 100 ml of water. The reaction mixture was poured into 1.4 l of water and the resulting precipitate was collected on a filter, washed with water, air dried to obtain 28 g (87 mole %) of (I). Recrystallization from acetone gave pure (I) as yellow crystals, mp 247°–249° C., Anal. Calcd. for $C_{17}H_{10}O_5$: C, 69.39; H, 3.42. Found: C, 68.86; H, 3.47. Molecular weight calculated 294, found 304. The proton and $^{13}C$ nmr spectra, the infrared spectrum, and the mass spectrum of (I) confirmed the formulation.

EXAMPLE II 2-(Vinylphenyl)-3-phenylmaleic anhydride (II) was prepared in the manner of Example (I) using a mixture of 3- and 4-vinylphenylacetic acid (4.86 g, 0.03 mole) and 6.9 g of mixed sodium and potassium salts of benzoylformic acid (0.03 mole of benzoylformate). The vinylphenylacetic acid was prepared from a 60:40 mixture of 3- and 4-vinylbenzyl cyanide by the method of U.S. Pat. No. 3,073,862, Example 1. Compound (II) was isolated as yellow crystals, mp 89°–92° C. Anal. Calcd. for $C_{18}H_{15}O_3$: C, 78.3; H, 4.4. Found: C 76.1; H, 4.5. The $^{13}C$ nmr spectrum confirmed the formulation of (II) as a 25:75 mixture of the 3-:4-isomers.

EXAMPLES III–XXX

In the procedure of Example I di-substituted maleic anhydride compounds (III)–(XXX) of the following structure

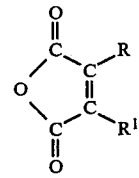

were prepared by modified Perkin condensation of one equivalent of an alkali metal salt of an alpha-keto acid of formula $RCOCO_2H$ and one equivalent of an acetic acid compound of formula $R^1CH_2CO_2H$.

| Example | R | $R^1$ | Color | Yield Mole % | M.P. °C. |
| --- | --- | --- | --- | --- | --- |
| III | $C_6H_5$ | 4-$(CH_3CONH)C_6H_4$ | Y | 61 | 192–195 |
| IV | $C_6H_5$ | 4-$(CH_3CO_2)C_6H_4$ | Y | 78 | 142–144 |
| V | $C_6H_5$ | 4-$(HO_2CCH_2O)C_6H_4$ | Y-G | 77 | 138–140 |

-continued

| Example | R | R$^1$ | Color | Yield Mole % | M.P. °C. |
|---|---|---|---|---|---|
| VI | C$_6$H$_5$ | 4-BrC$_6$H$_4$ | Y | 78 | 127–128 |
| VII | C$_6$H$_5$ | 2-(HO$_2$C)C$_6$H$_4$ | W | 70 | 224–226 |
| VIII | C$_6$H$_5$ | 3-(HO$_2$C)C$_6$H$_4$ | Y | 71 | 236–237 |
| IX | C$_6$H$_5$ | 4-CH$_3$C$_6$H$_4$ | Y | 83 | 125–126 |
| X | C$_6$H$_5$ | 4(CH$_3$O)C$_6$H$_4$ | Y | 89 | 136–137 |
| XI | C$_6$H$_5$ | 3,4-(CH$_3$O)$_2$C$_6$H$_3$ | Y | 70 | 114–115 |
| XII | C$_6$H$_5$ | 2-naphthyl | Y | 81 | 127–130 |
| XIII | C$_6$H$_5$ | 2-thienyl | Y | 50 | 150–151 |
| XIV | C$_6$H$_5$ | 1 H—indole-2-yl | Y | 69 | 170–172 |
| XV | C$_6$H$_5$ | C$_6$H$_5$S | Y | 50 | 83–85 |
| XVI | C$_6$H$_5$ | 4-(CH$_3$)C$_6$H$_4$S | Y | 48 | 116–117 |
| XVII | C$_6$H$_5$ | 2-(HO$_2$C)C$_6$H$_4$S | T | 39 | 260–263, dec. |
| XVIII | C$_6$H$_5$ | C$_6$H$_5$SO$_2$ | Y | 48 | 179–180 |
| XIX | C$_6$H$_5$ | 4-O$_2$NC$_6$H$_4$ | T | 80 | 124–126 |
| XX | 4-t-C$_4$H$_9$C$_6$H$_4$ | C$_6$H$_5$ | Y | 75 | 94–95 |
| XXI | 3,4-(CH$_3$)$_2$C$_6$H$_4$ | C$_6$H$_5$ | Y-G | 70 | 106–108 |
| XXII | C$_6$H$_5$CH=CH | C$_6$H$_5$ | Y-O | 51 | 135–136 |
| XXIII | C$_6$H$_5$CH=CH | C$_6$H$_5$CH=CH | O-R | 30 | 132–135 |
| XXIV | C$_6$H$_5$CH=CH | 2-(HO$_2$C)C$_6$H$_4$ | Y | 48 | 116–117 |
| XXV | 4-OHCC$_6$H$_4$CH=CH | C$_6$H$_5$ | Y-O | 65 | 160–162 |
| XXVI | 2-furyl-CH=CH— | C$_6$H$_5$ | GD | 84 | 179–181 |
| XXVII | 2-furyl-CH=CH | 2-(HO$_2$C)C$_6$H$_4$ | Y | 70 | 249–250 |
| XXVIII | 2-thienyl-CH=CH— | C$_6$H$_5$ | GD | 80 | 190–191 |
| XXIX | 2-thienyl | 2-thienyl | Y | 66 | 114–115 |
| XXX | phthalic anhydride | C$_6$H$_5$ | Y | 42 | >210, dec. |

Note:
Y — yellow;
W — white;
O — orange;
R — red;
G — green;
GD — gold;
T — tan

EXAMPLE XXXI 2-(4-aminophenyl)-3-phenylmaleic anhydride (XXXI) was prepared by stirring and refluxing 4.0 g of the product of Example III with 0.26 moles of NaOH dissolved in a mixture of 100 ml of water and 50 ml of methanol for 2 hours. When the mixture was cooled to 15° C. and acidified to a pH of 1 with concentrated hydrochloric acid, 3.04 g of compound (XXXI) precipitated as a red solid. It melted to form a glass at 65° C. which decomposed above 350° C. The formulation was confirmed by proton and $^{13}$C nmr and infrared spectroscopy and by mass spectrometry.

EXAMPLE XXXII 2-(4-Hydroxyphenyl)-3-phenylmaleic anhydride (XXXII) was prepared from the product of Example IV in the manner of Example XXXI. Compound XXXII was isolated as gold colored crystals, mp 191°–193° C. Anal. Calcd. for C$_{16}$H$_{10}$O$_4$: C, 72.18; H, 3.79. Found: C, 72.10; H, 3.47. The infrared spectrum, and proton and $^{13}$C nmr spectra confirmed the formulation.

EXAMPLE XXXIII 2-(4-Acetoxyphenyl)-3-methylmaleic anhydride (XXXIII) was prepared in the following manner. A one liter round-bottom flask was charged with 60.9 g (0.40 mole) of 4-hydroxphenylacetic acid, 17 g (0.40 mole) of sodium hydroxide, and 100 ml of water. The water was then evaporated and a magnetic stirring bar and 350 ml of acetic anhydride was added to the resulting sodium salt of 4-hydroxphenylacetic acid. After stirring for 20 minutes, 40.0 g of pyruvic acid was added, stirred at room temperature for 15 minutes, and stirred at reflux for an hour. Cooling and adding 1500 ml of water gave a yellow precipitate which was collected on a filter, washed with water, air dried, and recrystallized from ethanol to give 30.0 g (30 mole %) of (XXXIII) as pale yellow crystals, mp 108°–109° C. Anal. Calcd. for C$_{13}$H$_{10}$O$_5$: C, 63.42; H, 4.09. Found: C, 63.38; H, 4.16.

The proton and $^{13}$C nmr spectra and the infrared spectrum of (XXXIII) confirmed the formulation.

EXAMPLES XXXIV–XXXX

In the procedure of Example XXXIII di-substituted maleic anhydride compounds (XXXIV)–(XXXX) of the following structure

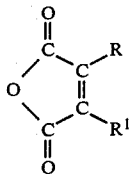

were prepared by modified Perkin condensation of one equivalent of an alpha-keto acid compound formula $RCOCO_2H$ with an acetic anhydride slurry of one equivalent of an alkali metal salt compound of formula $R^1CH_2CO_2H$.

| Example | R | R$^1$ | Color | Yield Mole % | M.P. °C. |
|---|---|---|---|---|---|
| XXXIV | CH$_3$ | 4-(CH$_3$CONH)C$_6$H$_4$ | GD | 50 | 171–172 |
| XXXV | CH$_3$ | 4-(CH$_3$CO$_2$)C$_6$H$_4$ | Y | 39 | 108–109 |
| XXXVI | CH$_3$ | 2-naphthyl | Y | 48 | 179–180 |
| XXXVII | CH$_3$ | 2-thienyl | | | 138–139 |
| XXXVIII | CH$_3$ | 2-HO$_2$C(C$_6$H$_4$) | T | 28 | 213–215, dec. |
| XXXIX | (CH$_3$)$_2$CHCH$_2$ | C$_6$H$_5$ | Y | 42 | oil |
| XXXX | (CH$_3$)$_2$CH | C$_6$H$_5$ | W | 35 | 121–122 |

EXAMPLE XXXXI

In the procedure of Example XXXI 2-(4-hydroxyphenyl)-3-methylmaleic anhydride (XXXXI) was prepared from the product of Example XXXIII in 92 mole % yield, mp 166°–168° C. Anal. Calcd. for $C_{11}H_8O_4$: C, 64.71; H, 3.95. Found: C, 63.42; H, 4.09. Molecular weight (vapor pressure osmometry) calcd. 204, found 202. The infrared spectrum and proton and $^{13}$C nmr spectra of (XXXXI) confirmed the formulation.

EXAMPLES XXXXII–LIII

In the procedure of Example I bis(di-substituted maleic anhydride) compounds (XXXXII–LIII) of formula

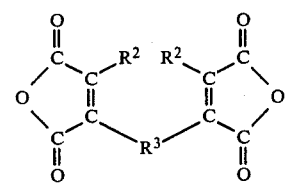

were prepared by modified Perkin condensation of two equivalents of an alkali metal salt of an alpha-keto acid of formula $R^2COCO_2H$ and one equivalent of a bis(acetic acid) compound of formula $R^3(CH_2CO_2H)_2$.

| Example | R$^2$ | R$^3$ | Color | Yield Mole % | M.P. °C. |
|---|---|---|---|---|---|
| XXXXII | C$_6$H$_5$ | 1,4-C$_6$H$_4$ | Y | 74 | 264–266 |
| XXXXIII | C$_6$H$_5$ | 1,3-C$_6$H$_4$ | Y | 56 | 188–190 |
| XXXXIV | C$_6$H$_5$ | naphthyl | Y | 76 | 304–305 |
| XXXXV | C$_6$H$_5$ | -C$_6$H$_4$-O-C$_6$H$_4$- | Y | 77 | 198–200 |
| XXXXVI | C$_6$H | -S-C$_6$H$_4$-S- | Y | 40 | 212–214 |
| XXXXVII | C$_6$H$_5$ | -C$_6$H$_4$-N=N-C$_6$H$_4$- | O | 79 | 319–321 |
| XXXXVIII | 4-t-C$_4$H$_9$C$_6$H$_5$ | 1,4-C$_6$H$_4$ | Y | 70 | 295–296 |
| XXXXIX | C$_6$H$_5$CH=CH | 1,4-C$_6$H$_4$ | | 81 | 268–269 |
| L | C$_6$H$_5$CH=CH | 1,3-C$_6$H$_4$ | O | 71 | 235–236 |
| LI | 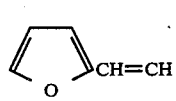 | 1,4-C$_6$H$_4$ | R | 65 | >300, dec. |

| Example | R² | R³ | Color | Yield Mole % | M.P. °C. |
|---|---|---|---|---|---|
| LII | (thiophene-CH=CH) | 1,4-C₆H₄ | R | 77 | 286–287 |
| LIII | C₆H₅ | (2,6-dimethylphenyl-4-yl) | Y | 71 | 289–290 |

EXAMPLE LIV–LVI

In the procedure of Example XXXIII, bis(di-substituted maleic anhydride) compounds (LIV)–(LVI) of formula

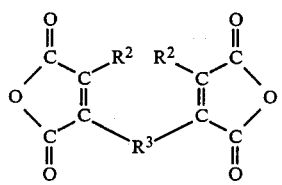

were prepared by modified Perkin condensation of two equivalents of an alpha-keto acid compound of formula R²COCO₂H with an acetic anhydride slurry of one equivalent of a alkali metal salt of bis(acetic acid) compound of formula R³(CH₂CO₂H)₂.

| Example | R | R² | Color | Yield Mole % | M.P. °C. |
|---|---|---|---|---|---|
| LIV | CH₃ | 1,4-C₆H₄ | W | W | 223–224 |
| LV | CH₃ | (naphthalene) | Y | 43 | 265–266 |
| LVI | CH₃ | (2,4,6-trimethylphenyl) | W | 22 | 251–253 |

EXAMPLE LVII

3-Carboxyphenanthrene-9,10-dicarboxylic anhydride (LVII) was prepared as follows. An Ace-Hanovia photochemical reactor was equipped with a magnetic stirring bar, a water-cooled condenser, and a thermometer. The reactor was charged with (I) (8.0 g, 0.034 mole), iodine (0.02 g, 0.08 mmole), and 300 ml of acetone. A water-jacketed vycor immersion well containing a 450 Watt medium-pressure mercury vapor lamp was fitted within the reactor well and the orange solution was irradiated for 16 hours while air was bubbled at 50 ml/min through the solution. The solid that precipitated was collected on a filter, washed with acetone, and air dried to yield 6.40 g (81 mole %) of (LVII) as a yellow powder, mp 375°–377° C. Anal. Calcd. for C₁₇H₈O₅: C, 69.87; H, 2.76. Found: C, 69.56; H, 2.89. The infrared and proton and ¹³C nmr spectra confirmed the formulation.

EXAMPLES LVIII–LX

In the procedure of Example LVII, substituted phenanthrene-9,10-dicarboxylic anhydride compounds (LVIII)–(LX) of the structure

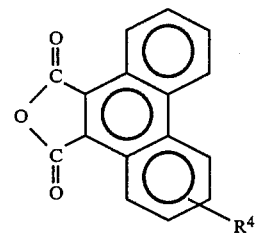

were prepared by photo-oxidation of the corresponding disubstituted maleic anhydrides.

| Example | R⁴ | Color | Yield Mole % | M.P. °C. |
|---|---|---|---|---|
| LVIII | 2-COOH | Y | 50 | >360, dec. |
| LIX | 1-COOH | W | 29 | 277–280 |
| LX | 3-OOCCH₃ | Y | 36 | 247–248 |

EXAMPLE LXI

3-Hydroxyphenanthrene-9,10-dicarboxylic anhydride (LXI) was prepared from compound (LX) by hydrolysis with sodium hydroxide and acidification in the method of Example XXXI. Compound (LXI) was isolated as yellow crystals in 84 mole % yield, mp 380°–382° C. Anal. Calcd. for C₁₆H₈O₄: C, 72.73; H, 3.05. Found, C, 70.48; H, 3.10. The infrared spectrum and the proton and ¹³C nmr spectra of (LXI) confirmed the formulation.

EXAMPLE LXII

In the method of Example LVII the product of Example XXXXII was photo-oxidized to give a 26 mole % yield of dibenz[a,h]anthracene-5,6:12,13-tetracarboxylic acid dianhydride (LXII) as a yellow-orange powder, mp 402° C. with decomposition. Anal. Calcd. for C₂₆H₁₀O₆: C, 74.64; H, 2.41. Found: C, 73.89; H, 2.61. The formulation of (LXII) was confirmed by high resolution mass spectrometry.

EXAMPLE LXIII

In the method of Example LXII the product of Example XXXXIII was photo-oxidized to give a 57 mole % yield of dibenz[a,j]anthracene-5,6:8,9-tetracarboxylic acid dianhydride (LXIII) as a yellow powder, mp 375° C. with decomposition. Anal. Calcd. for C₂₆H₁₀O₆: C, 74.64; H, 2.41. Found: C, 71.90; H, 2.99. The formulation of (LXIII) was confirmed by high resolution mass spectrometry.

EXAMPLE LXIV

A polyamide-imide of (I) and oxybisaniline was prepared as follows. The acid chloride of anhydride-acid (I) was prepared by refluxing (I) in an excess of thionyl chloride containing one drop of N,N'-dimethylformamide (DMF) as a catalyst for 24 hours. The thionyl chloride was then removed by distillation at atmospheric pressure. The anhydride-acid chloride was then distilled as a golden oil by vacuum pump distillation at about 170° C. The oil solidified to a glass on cooling to room temperature. A 100 ml, 3-neck round-bottom flask was equipped with a magnetic stirring bar, a nitrogen inlet and a reflux condenser fitted with a Dean-Stark condenser and a drying tube. The flask was charged with oxybis(aniline) (OBA) (4.53 g, 0.0226 mmole) and 20 ml of N-methylpyrrolidinone (NMP). To this was added 21.42 g of a 33.0 wt% solution of anhydride-acid chloride of (I) (7.07 g, 0.0226 mmole) in NMP. An additional 10 ml of xylene and 10 ml of NMP was added. The reaction mixture was stirred at room temperature for 15 minutes, and then heated to about 145° C. to remove the water of reaction as a xylene azeotrope. The xylene was then distilled from the reaction and the NMP solution was heated to reflux for an additional 2.5 hours. The solution was cooled below 100° C. and slowly poured into about 200 ml water in a rapidly spinning blender. The resulting white precipitate of polyamide-imide (LXIV) was collected on a filter, washed thoroughly with water, and air dried overnight. After drying at 190° C./0.1 torr for six hours 10.2 g (98.5 mole %) of (LXIV) was obtained with inherent viscosity, measured in 60:40 phenol:tetrachloroethane, of 0.59 dl/g. The polymer has a glass transition temperature of 263° C. and decomposition temperature of greater than 350° C. No melt temperature was detected. Anal. Calcd. for $C_{29}H_{18}N_2O_4$: C, 75.97; H, 3.96; N, 6.11. Found C, 74.56; H, 4.23; N, 3.74.

EXAMPLE LXV

A copolymer of 0.1 g of 2-(vinylphenyl)-3-phenylmaleic anhydride (II) and styrene was prepared. A mixture of freshly distilled styrene (4.9 g), 0.1 g of (II), and 0.05 g of benzoyl peroxide was heated at 80° C. for 16 hours. The polymer was dissolved in 50 ml of benzene and poured with stirring into 200 ml of methanol. This purification was repeated to give 4.8 g of copolymer (LXV) as a light yellow powder, inherent viscosity 0.58. The polymer showed the anhydride carbonyl bands in the infrared spectrum at 1830 and 1770 $cm^{-1}$.

EXAMPLE LXVI

A polyimide of dianhydride (XXXXII) and oxybisaniline was prepared. A 200 ml, 3-neck round-bottom flask was equipped with a mechanical stirrer, a nitrogen inlet, and a Dean-Stark trap fitted with a reflux condenser. The flask was flushed with nitrogen and charged with oxybis(aniline) (OBA) (2.10 g, 0.100 mole), 35 ml of N-methyl-2-pyrrolidinone (NMP), and 10 ml of xylene. While stirring the solution vigorously 4.22 g (0.100 mole) of 3,3'-(1,4-phenylene)bis(2-phenylmaleic anhydride) (XXXXII) and an additional 10 ml of NMP was added to this solution all at once. After 20 minutes, the temperature of the reaction was brought to reflux and the water of imidization was removed as a xylene azeotrope for about 75 minutes. The Dean-Stark trap was drained and the xylene was distilled from the reaction. The NMP solution was refluxed for an additional two hours. The solution was cooled below 100° C. and slowly poured into about 200 ml water in a rapidly spinning blender. The polyimide was washed thoroughly with water, air dried overnight, and vacuum dried at 150° C./250 torr overnight to yield 95 mole% of polyimide (LXVI) as a bright yellow powder. Anal. Calcd. for $C_{38}H_{22}N_2O_5$: C, 77.81; H, 3.78; N, 4.78. Found: C, 77.35; H, 4.06; N, 4.97. The inherent viscosity, measured in 60:40 phenol:tetrachloroethane was 0.66 dl/g. The glass transition temperature was 269° C. and the catastrophic decomposition temperature was greater than 410° C.

EXAMPLE LXVII

Conductive polymer films of polyimide (LXVI) were prepared. Films were cast on glass plates from a 8 wt% solution of polyimide (LXVI) in N-methyl-2-pyrollidinone (NMP) by vacuum drying the solution at 160° C./250 torr for 1.5 hours. Pieces of the amber film measuring 1.5×4 cm were placed in a quartz tube and heated in slow flow of nitrogen to either 750° C. (LXVIIa) or 850° C. (LXVIIb) over about 30 minutes. The final temperature was maintained for about 40 minutes. When cooled, the films shrunk to about one-third their original size. They were still intact although bubbles were apparent on their surface. Conductivity of the pyrolyzed films was measured with an Alessi Industries four point probe employing a Keithly Instruments 225 Current Source and a Keithly Instruments 610 C Electrometer and are shown below.

| Material | Pyrolysis Temperature (°C.) | Current (amps) | Voltage (volts) | Cf |
|---|---|---|---|---|
| (LXVI) | none | $3 \times 10^{-9}$ | 29 | 0.13 |
| (LXVIIa) | 750 | 0.01 | 0.25 | 0.6 |
| (LXVIIb) | 850 | 0.1 | 0.35 | 0.4 |

| Material | Resistivity (ohm-cm) | Conductivity $(ohm-cm)^{-1}$ |
|---|---|---|
| LXVI | $8 \times 10^9$ | $1.2 \times 10^{-10}$ |
| LXVIIa | 94 | 0.0106 |
| LXVIIb | 8.8 | 0.11 |

Cf = a correction factor for the thickness of the films

EXAMPLES LXVIII–LXX

The procedure of Example LXVI was used prepare polyimides (LXVIII–LXX) from one equivalent of bis(di-substituted maleic anhydride) (XXXXII) or (XXXXIII) and diamines according to the equation

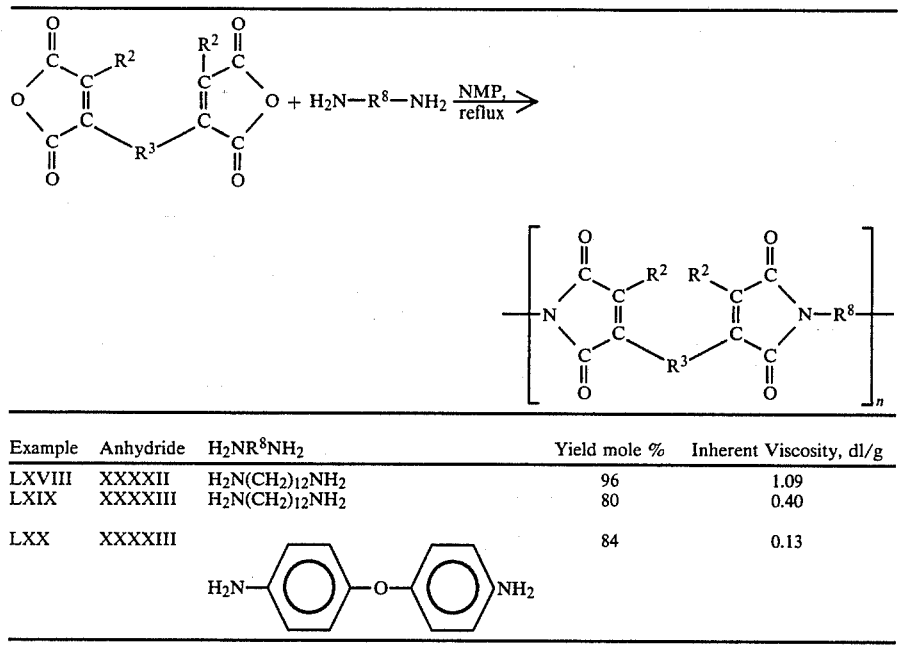

| Example | Anhydride | H$_2$NR$^8$NH$_2$ | Yield mole % | Inherent Viscosity, dl/g |
|---|---|---|---|---|
| LXVIII | XXXXII | H$_2$N(CH$_2$)$_{12}$NH$_2$ | 96 | 1.09 |
| LXIX | XXXXIII | H$_2$N(CH$_2$)$_{12}$NH$_2$ | 80 | 0.40 |
| LXX | XXXXIII | H$_2$N—⟨phenyl⟩—O—⟨phenyl⟩—NH$_2$ | 84 | 0.13 |

| | Elemental Analysis Found (Calcd) | | |
|---|---|---|---|
| | C | H | N |
| LXVIII | 77.57 (77.79) | 6.47 (6.53) | 4.71 (4.77) |
| LXIX | 77.56 (77.79) | 6.63 (6.53) | 5.00 (4.77) |
| LXX | 76.10 (77.18) | 3.98 (3.78) | 4.33 (4.78) |

EXAMPLE LXXI

Polymer film of polyimide LXVI were prepared in the manner of Example LXVII. The film was cured at 250° C. in a slow nitrogen flow for 4 hours to give a tough amber material about 2 mil thick. It is unaffected by water vapor at 150° C. for more than 6 weeks and suffered no evident loss of strength after exposure to water vapor for more than 4 hours at 250° C. The film resists basic hydrolysis. It was unaffected by 10% aqueous sodium hydroxide solution at room temperature for more than one week.

What is claimed is:

1. A substituted phenanthrene anhydride compound of the structural formula

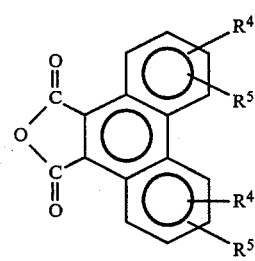

wherein R$^4$ and R$^5$ are individually selected from the group consisting of —NH$_2$ and —CH=CH$_2$.

2. A substituted dibenzanthracene dianhydride compound of the structural formula

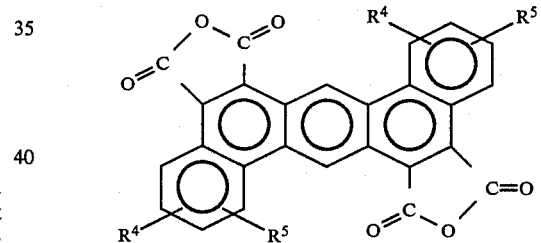

wherein R$^4$ and R$^5$ are individually selected from the group consisting of hydrogen, alkyl moieties of 1 to 10 carbon atoms, phenyl moieties, naphthyl moieties, —NO$_2$, —NHCOCH$_3$, —NH$_2$, —OCOCH$_3$, —OH, —OCH$_3$, —CH=CH$_2$, —COOCH$_3$ and —COOH.

3. A substituted dibenzanthracene dianhydride compound of the structural formula

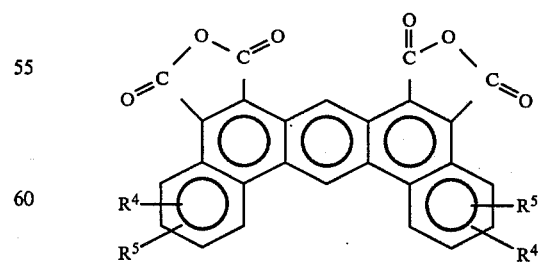

wherein R$^4$ and R$^5$ are individually selected from the group consisting of hydrogen, alkyl moieties of 1 to 5 carbon atoms, phenyl moieties, naphthyl moieties, —NO$_2$, —NHCOCH$_3$, —NH$_2$, —OCOCH$_3$, —OH, —OCH$_3$, —CH=CH$_2$, —COOCH$_3$, and —COOH.

* * * * *